United States Patent [19]

Rody et al.

[11] 4,237,297
[45] Dec. 2, 1980

[54] PIPERIDINE CONTAINING MALONIC ACID DERIVATIVES

[75] Inventors: Jean Rody, Riehen; Friedrich Karrer, Zofingen, both of Switzerland

[73] Assignee: Ciba-Geigy Corporation, Ardsley, N.Y.

[21] Appl. No.: 91,630

[22] Filed: Nov. 5, 1979

Related U.S. Application Data

[63] Continuation of Ser. No. 963,537, Nov. 24, 1978.

[30] Foreign Application Priority Data

Dec. 2, 1977 [CH] Switzerland .................. 14769/77

[51] Int. Cl.³ .......................................... C07D 401/12
[52] U.S. Cl. .................................. 546/189; 546/188; 546/190; 260/45.8 NT
[58] Field of Search ............... 546/188, 189, 190

[56] References Cited

U.S. PATENT DOCUMENTS

| 3,640,928 | 2/1972 | Murayama et al. | 546/189 |
| 3,993,655 | 11/1976 | Rasberger et al. | 546/189 |
| 4,148,783 | 4/1979 | Rasberger et al. | 546/188 |
| 4,148,784 | 4/1979 | Malherbe et al. | 546/189 |
| 4,154,722 | 5/1979 | Malherbe et al. | 546/190 |

FOREIGN PATENT DOCUMENTS

| 2258752 | 6/1973 | Fed. Rep. of Germany | 546/188 |
| 2647452 | 5/1977 | Fed. Rep. of Germany | 546/188 |
| 2718458 | 11/1977 | Fed. Rep. of Germany | 546/188 |

*Primary Examiner*—Henry R. Jiles
*Assistant Examiner*—Robert T. Bond
*Attorney, Agent, or Firm*—Luther A. R. Hall

[57] ABSTRACT

Malonic acid derivatives of the formula

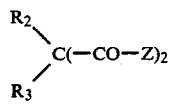

wherein Z contain sterically hindered piperidines as stabilizers against light-induced degradation for organic material.

5 Claims, No Drawings

PIPERIDINE CONTAINING MALONIC ACID DERIVATIVES

This is a continuation of application Ser. No. 963,537 filed on Nov. 24, 1978.

The present invention relates to new malonates, processes for their production, their use as stabilisers, and to the organic material stabilised therewith against light-induced degradation.

Malonates of sterically hindered 4-hydroxy-piperidines are known as stabilisers for synthetic polymers from U.S. Pat. No. 3,640,928 and British patent specification No. 1,399,239. These stabilisers have properties which become troublesome in their technical use, for example as regards stability to hydrolysis, volatility, extraction resistance and exudation resistance. Sterically hindered 4-hydroxy-piperidines are also known from German Offenlegungsschrift No. 2,456,864 as stabilisers for synthetic polymers. In their technical use, however, excessive heating, which can also occur unintentionally during the incorporation or processing, or for example their admixture as melt via a screw to the extruder, gives rise to discolourations which are often undesirable.

Starting from this state of the art, it was the object of the invention to provide stabilisers for organic material which do not have the drawbacks of the known stabilisers or have them only to a substantially lesser extent.

The invention relates to malonic acid derivatives of the formula I,

wherein $R_2$ is $C_1$–$C_{12}$alkyl, $C_3$–$C_4$alkenyl, benzyl, or phenyl which is unsubstituted or substituted by $C_1$–$C_8$alkyl or $C_1$–$C_8$alkoxy, or is cyano, $R_3$ is $C_1$–$C_{12}$alkyl, $C_3$–$C_4$alkenyl or benzyl, and Z is a group of the formula II or III

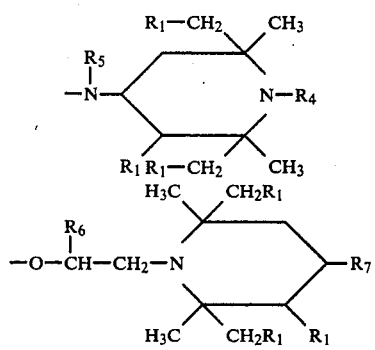

wherein $R_1$ is hydrogen or $C_1$–$C_4$alkyl, $R_4$ is hydrogen, O·, —OH, alkyl of 1 to 12 carbon atoms, alkenyl of 3 or 4 carbon atoms, propargyl, benzyl or a group of the formula —CH$_2$—CH(OR$_9$)—R$_8$, wherein $R_8$ is hydrogen, methyl or phenyl, and $R_9$ is hydrogen or a group A—CO—; or $R_4$ represents a group A—CO— and in both cases A represents alkyl of 1 to 18 carbon atoms, alkenyl of 2 or 3 carbon atoms, cyclohexyl, phenyl, benzyl, a phenyl, phenylmethyl or phenylethyl group which is substituted by 1 or 2 alkyl groups, each containing 1 to 4 carbon atoms, and by a hydroxyl group, or represents alkylamino of 1 to 12 carbon atoms, dialkylamino of 2 to 16 carbon atoms, anilino, alkoxy of 1 to 12 carbon atoms, benzyloxy or phenoxy, $R_5$ is hydrogen, alkyl of 1 to 18 carbon atoms, alkenyl of 3 to 4 carbon atoms, propargyl, cycloalkyl of 5 to 12 carbon atoms, aralkyl of 7 to 14 carbon atoms which can be substituted by OH, or represents a group of the formula IV

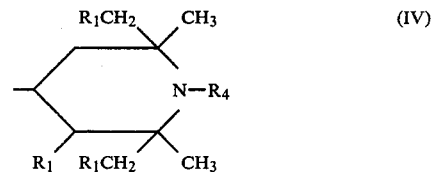

$R_6$ is hydrogen, methyl, ethyl or phenyl, $R_7$ represents hydrogen, —OR$_{10}$ or —N(R$_{11}$)(R$_{12}$), and $R_{10}$ represents alkyl of 1 to 18 carbon atoms, alkenyl of 3 to 4 carbon atoms, benzyl, 2-cyanoethyl, an aliphatic, cycloaliphatic, aromatic or araliphatic acyl group of not more than 18 carbon atoms which can be substituted in the aromatic moiety by halogen, alkoxy of 1 to 4 carbon atoms, alkyl of 1 to 4 carbon atoms and/or hydroxyl, $R_{11}$ represents alkyl of 1 to 18 carbon atoms, alkenyl of 3 to 4 carbon atoms or phenylalkyl of 7 to 9 carbon atoms, and $R_{12}$ has the same meaning as $R_{11}$ or represents an aliphatic, cycloaliphatic, aromatic or araliphatic acyl group of not more than 18 carbon atoms which can be substituted in the aromatic moiety by halogen, alkoxy of 1 to 4 carbon atoms, alkyl of 1 to 4 carbon atoms and/or hydroxyl, and the salts thereof.

As $C_1$–$C_4$alkyl, $R_1$ is branched or especially unbranched alkyl, such as ethyl, n-propyl or n-butyl, but is primarily methyl. Preferably, $R_1$ is hydrogen. All substituents $R_1$ are identical.

As $C_1$–$C_{12}$alkyl, $R_2$ and $R_3$ are branched or unbranched alkyl, especially $C_2$–$C_8$alkyl, such as ethyl, n-propyl or isopropyl, n-butyl or isobutyl, a pentyl, hexyl, heptyl or octyl radical, such as n-octyl or isooctyl. The same applies to $R_4$ as alkyl, whilst alkyl represented by $R_5$, A, $R_{10}$ and $R_{11}$ can be in addition for example tridecyl, hexydecyl or octadecyl.

As $C_3$–$C_4$alkenyl, $R_2$ and $R_3$ are in particular methallyl, primarily allyl. The same applies to $R_4$, $R_5$, $R_{10}$ and $R_{11}$. Alkenyl represented by A is in particular vinyl or allyl.

As phenyl substituted by $C_1$–$C_8$alkyl, $R_2$ is in particular phenyl which is substituted by ethyl, n-propyl or isopropyl, but preferably by methyl; and as phenyl substituted by $C_1$–$C_8$alkoxy, $R_2$ is phenyl substituted by ethoxy, n-propoxy or isopropoxy, but preferably by methoxy. Preferably, however, $R_2$ is unsubstituted.

If $R_2$ and $R_3$ are alkyl, both together should not contain a tertiary α-carbon atom. Thus where $R_2$ and $R_3$ are alkyl, at least one of these substituents has a primary or secondary α-carbon atom.

As phenylalkyl of 7 to 9 carbon atoms, $R_{11}$ and $R_{12}$ are for example benzyl, phenylethyl or phenylpropyl. $R_5$ as aralkyl of 7 to 14 carbon atoms can furthermore also be, for example, diphenylylmethyl, naphthylpropyl or diphenylmethyl.

A group A—CO— represented by $R_4$ and/or $R_9$ can be, depending on the meaning of A, a carboxylic acid radical, for example acetyl, propionyl, butyryl, caprynyl, capryloyl, lauroyl, acryloyl, crotonyl, phenylacetyl-, β-(3,5-di-tert-butyl-4-hydroxyphenyl)-propionyl and -acetyl or benzoyl; or a carbamoyl radical, for example methylcarbamoyl, butylcarbamoyl, dodecylcarbamoyl, diethylcarbamoyl, dihexylcarbamoyl, dioctylcarbamoyl or phenylcarbamoyl; or a carboxylic acid ester radical, for example ethoxycarbonyl, isopropoxycarbonyl, 2-ethylhexyloxycarbonyl, dodecyloxycarbonyl, benzyloxycarbonyl or phenoxycarbonyl.

An aliphatic, cycloaliphatic, aromatic or araliphatic acyl group of not more than 18 carbon atoms represented by $R_{10}$ and/or $R_{11}$ which can be substituted in the aromatic moiety by halogen, alkoxy, alkyl or hydroxyl can be for example acetyl, propionyl, isobutyryl, capronyl, capryloyl, lauroyl, stearoyl, oleyl, cyclohexanecarbonyl, benzoyl, 4-chlorobenzoyl, toluoyl, 3-methoxybenzoyl, 2,4-dichlorobenzoyl, 4-tert-butylbenzoyl, phenylacetyl, 3,5-di-tert-4-hydroxybenzoyl or 4-chlorophenylpropionyl.

$R_5$ as cycloalkyl of 5 to 8 carbon atoms can be for example cyclopentyl, cyclohexyl or cyclooctyl. $R_{12}$ as cycloalkyl can furthermore also be, for example, cyclodecyl or cyclododecyl.

Preferred malonates are malonates Ia of the formula I, wherein
$R_1$ is hydrogen or methyl,
$R_2$ is $C_1$–$C_8$alkyl, allyl, methallyl, benzyl or phenyl,
$R_3$ is $C_2$–$C_8$alkyl, allyl, methallyl or benzyl,
Z is a group of the formula II or III,
$R_4$ is hydrogen, O·, alkyl of 1 to 8 carbon atoms, allyl, propargyl, benzyl, formyl, acetyl, acryloyl or crotonoyl,
$R_5$ is hydrogen, alkyl of 1 to 12 carbon atoms, cyclohexyl, benzyl or phenyl,
$R_6$ is hydrogen, methyl or ethyl,
$R_7$ is hydrogen or —$OR_{10}$ and $R_{10}$ represents hydrogen, alkyl of 1 to 6 carbon atoms, alkanoyl of 2 to 12 carbon atoms, benzoyl or benzyl.

Especially preferred malonates are malonates Ib of the formula I, wherein
$R_1$ is hydrogen or methyl,
$R_2$ is $C_1$–$C_8$alkyl, allyl, methallyl, benzyl or phenyl,
$R_3$ is $C_2$–$C_8$alkyl or benzyl,
Z is a group of the formula II or III,
$R_4$ is hydrogen, methyl, benzyl or acetyl,
$R_5$ is hydrogen or $C_1$–$C_4$alkyl, and
$R_6$ and $R_7$ are hydrogen.

The invention relates in particular to malonates Ic of the formula Ic, wherein
$R_1$ is hydrogen or methyl,
$R_2$ is $C_1$–$C_6$alkyl, allyl, methallyl or benzyl,
$R_3$ is benzyl, and
Z is a group of the formula II or III,
$R_4$ is hydrogen or methyl, and
$R_5$, $R_6$ and $R_7$ are hydrogen.

In the above malonates I and Ia to Ic, $R_2$ and $R_3$ are preferably benzyl. In addition, $R_1$ is preferably hydrogen.

Examples of malonates of the formula I are to be found in the Examples. These malonates are especially preferred.

The present invention also comprises the salts of compounds of the formula I which are formed by addition of acids in a maximum of amounts equivalent to the piperidine groups. Such acids can be inorganic acids, for example sulphuric, hydrochloric or phosphoric acid, organic carboxylic acids, such as formic, acetic, oxalic, maleic, benzoic or salicylic acid, organic sulphonic acids, such as methanesulphonic or p-toluenesulphonic acid, or organic phosphorus-containing acids, such as diphenylphosphoric acid, methanephosphoric acid or diphenylphosphinic acid.

The compounds of the formula I can be prepared by different multistep processes in which the individual process steps constitute reactions which are in themselves known.

To obtain the compounds of the formula I, a start is preferably made from compounds of the formula $CH_2(-COZ)_2$. Either firstly the substituent $R_2$ is introduced into these compounds and then the substituent $R_3$, or firstly the substituent $R_3$ and then the substituent $R_2$. If $R_2$ and $R_3$ are identical, then both can be introduced in one step.

The starting materials $CH_2(COZ)_2$ can be obtained by reaction of the corresponding lower alkyl esters $CH_2(COO\text{-alkyl})_2$ with the piperidine derivatives of the formula ZH. Examples of these latter compounds are 1,2,2,6,6-pentamethyl-4-aminopiperidine, 1-hydroxyethyl-2,2,6,6-tetramethyl-piperidine, 1-(2-hydroxypropyl)-2,2,6,6-tetramethyl-piperidine, or 1-(2-hydroxypropyl)-2,3,6-trimethyl-2,6-diethyl-4-acetoxypiperidine. Instead of the lower alkyl esters, it is also possible to react the corresponding acid chlorides $CH_2(COCl)_2$ with the piperidine derivatives.

The radical $R_2$ can be introduced in the manner of a malonic ester synthesis by converting a compound $CH_2(-COZ)_2$ into the alkali compound firstly by reaction with one equivalent of an alkali metal, alkali alcoholate, alkali amide, alkali hydride or a similar basic alkali compound, and then reacting the alkali compound with 1 mole of an $R_2$-halide, $R_2$Hal (Hal=chlorine, bromine or iodine), in the conventional manner.

The substituent $R_3$ must then be introduced into this $R_2$-malonic acid derivative. However, if $R_2$ is the same as $R_3$, then the introduction of both radicals can advantageously be effected simultaneously.

The introduction of the substituent $R_3$ can be accomplished by the classical method of C-alkylation of malonic acid derivatives, in which again the alkali compound is prepared initially and then reacted with a halogen compound, $R_3$Hal, wherein Hal once more represents chlorine, bromine or iodine. About 1 mole of a monohalide, $R_3$Hal, is used per mole of alkali compound. Examples of such halogen compounds are alkyl, alkenyl or benzyl halides.

Finally, the introduction of $R_4$ can also be effected together with the introduction of $R_3$ if $R_4$ and $R_3$ are identical, for example if they represent alkyl, alkenyl or benzyl.

In the light of these various possibilities of carrying out the individual reaction steps,
introduction of the piperidinyl radical,
introduction of the group $R_2$,
introduction of the group $R_3$,
and, optionally, the introduction of $R_4$,
the sequence of the individual steps will be so chosen as seems most appropriate in the individual case.

Advantageously, the above reaction of a malonic acid dialkyl ester with a piperidine derivative can also be carried out with a malonic ester which is substituted in the α-position by $R_2$ and $R_3$, the procedure being in particular as described above.

The starting materials are known or, if they are new, can be prepared by methods which are in themselves known and in analogy to known compounds.

The compounds of the formula I can be used according to the present invention as stabilisers for protecting plastics against damage by the action of oxygen, heat and light. Examples of such plastics are polyether-/polyesters as well as the polymers listed in German Offenlegungsschrift No. 2,456,864 on pages 12-14.

Of particular importance is the stabilising of polyolefins, styrene polymers and polyurethanes, for which the compounds of the formula I are preeminently suitable. Examples are polyethylene of high and low density, polypropylene, ethylene/polypropylene copolymers, polystyrene, styrene/butadiene/acrylonitrile copolymers, mixtures of polyolefins or of styrene polymers, polyurethanes based on polyethers or polyesters in the form of lacquers, elastomers or foam plastics.

The stabilisers are added to the plastics in a concentration of 0.01 to 5% by weight, based on the weight of the material to be stabilised. Preferably 0.03 to 1.5% by weight, most preferably 0.2 to 0.6% by weight, based on the weight of the material to be stabilised, is incorporated thereinto.

The incorporation can be effected after the polymerisation, for example by blending the compounds and optionally further additives into the melt by methods conventionally employed in the art, before or during the forming, or also by applying the dissolved or dispersed compounds to the polymer, optionally with subsequent evaporation of the solvent.

The new compounds can also be added to the plastics to be stabilised in the form of a masterbatch which contains these compounds in a concentration of 2.5 to 25% by weight. In the case of crosslinked polyethylene, the compounds are added before the crosslinking.

In addition to the compounds of the formula I other known stabilisers can also be added to the plastics. These can be for example antioxidants, UV absorbers or metal deactivators, or also costabilisers, for example of the phosphite type. Furthermore, it is also possible to add other substances conventionally employed in plastics technology, for example flame retardants, antistatic agents, plasticisers, lubricants, propellants, pigments, reinforcers or fillers.

Accordingly, the invention also relates to the plastics which are stabilised by the addition of 0.01 to 5% by weight of a compound of the formula I and which can contain, if desired, other known and customary additives. The stabilised plastics can be used in a very wide variety of forms, for example as sheets, filaments, ribbons, profiles, or as binders for lacquers, adhesives or cement.

The following Examples describe the production and use of the compounds of the present invention in more detail. Parts and percentages are by weight.

EXAMPLE 1

With stirring, 0.15 g of lithium amide is added to a solution, heated to 125° C., of 31.2 g of dimethyl dibenzylmalonate (m.p. 60°-61°) and 37.1 g of 1-(2-hydroxyethyl)-2,2,6,6-tetramethyl-piperidine (m.p. 96°-97° C.) in 300 ml of anhydrous xylene. The reaction mixture is then heated in the course of 3 hours to 136° C. while simultaneously introducing a weak flow of nitrogen, and the methanol which is set free and also xylene are distilled off over a descending cooler. The temperature is then raised to 150° C. and the bulk of the xylene is distilled off (duration about 4 hours). After cooling, the reaction mixture is dissolved in chloroform, washed repeatedly with water and dried over sodium sulphate. The solvent is completely distilled off in vacuo and the residue is crystallised in n-hexane, affording pure bis-[2-(2,2,6,6-tetramethyl-1-piperidinyl)-ethyl] dibenzylmalonate with a melting point of 77°-78° C. (Stabiliser 1).

EXAMPLE 2

By a procedure analogous to that described in Example 1, bis-[2-(2,2,6,6-tetramethyl-1-piperidinyl)-propyl] dibenzylmalonate (diastereoisomer mixture), with a melting point of about 85° C., is obtained from dimethyl dibenzylmalonate and 1-(2-hydroxypropyl)-2,2,6,6-tetramethyl-piperidine. (Stabiliser 2).

Calculated: C 76.1%; H 9.66%; N 4.33%. Found: C 75.9%; H 9.6%; N 4.5%.

EXAMPLE 3

By a procedure analogous to that described in Example 1, bis-[1-phenyl-2-(2,2,6,6-tetramethyl-1-piperidinyl)-ethyl] dibenzylmalonate (diastereoisomer mixture), with a melting point of about 140° C., is obtained from dimethyl dibenzylmalonate and 1-(2-hydroxy-2-phenylethyl)-2,2,6,6-tetramethyl-piperidine. (Stabiliser 3).

Calculated: C 79.23%; H 8.87%; N 3.62%. Found: C 79.4%; H 8.6%; N 3.6%.

EXAMPLE 4

With stirring, a solution of 20 g of benzylmalonic bis-(1,2,2,6,6-pentamethyl-4-piperidinyl)-amide in 50 ml of toluene and 100 ml of dimethylformamide is added dropwise in the course of about ½ hour to a suspension of oil-free sodium hydride (0.97 g) in toluene (20 ml). After the addition of the amide, the reaction mixture is stirred for a further 20 hours at 60° C. until all the sodium hydride is reacted. A solution of 7.7 g of benzyl bromide in 10 ml of toluene is then added dropwise to the reaction mixture at room temperature in the course of 40 minutes, the temperature is raised to 70° C. and stirring is continued for 12 hours at this temperature. For working up, the reaction solution is filtered warm to remove precipitated sodium bromide, the residue is washed well with chloroform and the combined filtrates are freed as completely as possible from all solvents by rotary evaporation. The residue is dissolved in 400 ml of chloroform, the solution is extracted repeatedly with water, dried over sodium sulphate and the solvent removed in vacuo. The crystalline residue is recrystallised once in toluene and once in benzene, affording dibenzylmalonic bis-(1,2,2,6,6-pentamethyl-4-piperidinyl)-amide with a melting point of 275°-277° C. (Stabiliser 4).

The benzylmalonic bis-(1,2,2,6,6-pentamethyl-4-piperidinyl)-amide used as starting material can be prepared by amidation of diethyl benzylmalonate with at least 2 equivalents of 4-amino-1,2,2,6,6-pentamethyl-piperidine at 130°-150° C. in the presence of a basic catalyst, for example lithium amide. Melting point: 242°-243° C.

EXAMPLE 5

By a procedure analogous to that described in Example 4, benzyl-n-octyl-malonic acid bis-(1,2,2,6,6-pentamethyl-4-piperidinyl)-amide, with a melting point of 164°–166° C., is obtained from benzylmalonic bis-(1,2,2,6,6-pentamethyl-4-piperidinyl)-amide and n-octylbromide. (Stabiliser 5).

EXAMPLE 6

100 parts of polypropylene powder (Moplen, fibre grade, available from Montedison) are homogenised with 0.2 part of octadecyl β-(3,5-ditert-butyl-4-hydroxyphenyl)propionate and 0.25 part of a stabiliser of Table 1 for 10 minutes at 200° C. in a Brabender plastograph. The resulting mass is removed from the kneader as quickly as possible and pressed to a sheet 2–3 mm thick in a toggle press. A portion of the crude moulding is cut out and pressed between two high-gloss rigid aluminium sheets in a laboratory press for 6 minutes at 260° C. and under a pressure of 40 kg/cm² to a sheet of 0.1 mm thickness, which is immediately chilled in cold water. Blanks each measuring 60×40 mm are then punched from this sheet and exposed with the respective exposure apparatus listed in the table. These mouldings are removed from the exposure apparatus at regular intervals of time and tested for their carbonyl content in an IR spectrophotometer. The increase in the carbonyl extinction at 5.85μ during the exposure is a yardstick for the photooxidative degradation of the polymer [see L. Balaban et al., H. Polymer Sci. Part C, 22, 1059–1071 (1969)] and, as experience shows, is connected with a decrease in the mechanical properties of the polymer. Thus, for example, the sheet is completely brittle on attaining a carbonyl extinction of about 0.300.

The protective action of the stabilisers of the invention can be observed from the following table:

TABLE 1

| Stabiliser | Exposure time in hours until CO extinction = 0.3 | Xenotest |
| --- | --- | --- |
| 1 | 4370 | 1200 |
| 2 | 2395 | 1200 |
| 3 | 3765 | 1200 |
| control | ~555 | 1200 |

EXAMPLE 7

By a procedure analogous to that of Example 1, dibenzylmalonic acid bis-[2-(2,2,6,6-tetramethyl-1-piperidinyl)-butyl] ester (diastereoisomer mixture) is obtained as a colourless resin from dimethyl dibenzylmalonate and 1-(2-hydroxybutyl)-2,2,6,6-tetramethylpiperidine (m.p. 109°–110° C.).

Analysis: Calculated: C 76.51%; H 9.86%; N 4.15%. Found: C 76.7%; H 10.1%; N 4.2%.

The ¹H—NMR spectrum accords well with the structure of the compound.

What is claimed is:

1. A compound of the formula I

wherein
$R_2$ is $C_1$–$C_{12}$alkyl, $C_3$–$C_4$alkenyl, benzyl, or phenyl which is unsubstituted or substituted by $C_1$–$C_8$alkyl or $C_1$–$C_8$alkoxy, or is cyano,
$R_3$ is $C_1$–$C_{12}$alkyl, $C_3$–$C_4$alkenyl or benzyl, and
Z is a group of the formula II or III

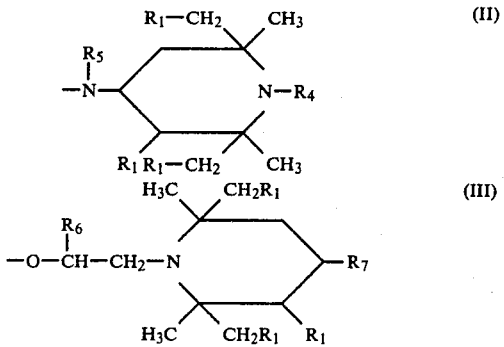

wherein
$R_1$ is hydrogen or $C_1$–$C_4$alkyl,
$R_4$ is hydrogen, O·, —OH, alkyl of 1 to 12 carbon atoms, alkenyl of 3 or 4 carbon atoms, propargyl, benzyl or a group of the formula —CH₂—CH(OR₉)—R₈, wherein $R_8$ is hydrogen, methyl, or phenyl, and $R_9$ is hydrogen or a group A—CO—; or $R_4$ represents a group A—CO— and in both cases A represents alkyl of 1 to 18 carbon atoms, alkenyl of 2 or 3 carbon atoms, cyclohexyl, phenyl, benzyl, a phenyl, phenylmethyl or phenylethyl group which is substituted by 1 or 2 alkyl groups, each containing 1 to 4 carbon atoms, and by a hydroxyl group, or represents alkylamino of 1 to 12 carbon atoms, dialkylamino of 2 to 16 carbon atoms, anilino, alkoxy of 1 to 12 carbon atoms, benzyloxy or phenoxy,
$R_5$ is hydrogen, alkyl of 1 to 18 carbon atoms, alkenyl of 3 to 4 carbon atoms, propargyl, cycloalkyl of 5 to 12 carbon atoms, aralkyl of 7 to 14 carbon atoms which can be substituted by OH, or represents a group of the formula IV

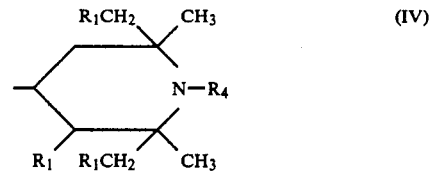

$R_6$ is hydrogen, methyl, ethyl or phenyl,
$R_7$ represents hydrogen, —OR₁₀ or —N(R₁₁)(R₁₂), and $R_{10}$ represents alkyl of 1 to 18 carbon atoms, alkenyl of 3 to 4 carbon atoms, benzyl, 2-cyanoethyl, an aliphatic, cycloaliphatic, aromatic or araliphatic carboxylic acyl group of not more than 18 carbon atoms which can be substituted in the aromatic moiety by halogen, alkoxy of 1 to 4 carbon atoms, alkyl of 1 to 4 carbon atoms and/or hydroxyl, $R_{11}$ represents alkyl of 1 to 18 carbon atoms, alkenyl of 3 to 4 carbon atoms or phenylalkyl of 7 to 9 carbon atoms, and $R_{12}$ has the same meaning as $R_{11}$ or represents an aliphatic, cycloaliphatic, aromatic or araliphatic carboxylic acyl group of not more than 18 carbon atoms which can be substituted in the aromatic moiety by halogen, alkoxy of 1 to 4 carbon atoms, alkyl of 1 to 4 carbon atoms and/or hydroxyl,
and the salts thereof.

2. A compound according to claim 1, wherein $R_1$ is hydrogen or methyl, $R_2$ is $C_1$–$C_8$alkyl, allyl, methallyl, benzyl or phenyl,
$R_3$ is $C_2$–$C_8$alkyl, allyl, methallyl or benzyl,
Z is a group of the formula II or III,
$R_4$ is hydrogen, O·, alkyl of 1 to 8 carbon atoms, allyl, propargyl, benzyl, formyl acetyl, acryloyl or crotonyl,
$R_5$ is hydrogen, alkyl of 1 to 12 carbon atoms, cyclohexyl, benzyl or phenyl,
$R_6$ is hydrogen, methyl or ethyl,
$R_7$ is hydrogen or —$OR_{10}$ and $R_{10}$ represents hydrogen, alkyl of 1 to 6 carbon atoms, alkanoyl of 2 to 12 carbon atoms, benzoyl or benzyl.

3. A compound according to claim 1, wherein
$R_1$ is hydrogen or methyl,
$R_2$ is $C_1$–$C_8$alkyl, allyl, methallyl, benzyl or phenyl,
$R_3$ is $C_2$–$C_8$alkyl, or benzyl,
Z is a group of the formula II or III,
$R_4$ is hydrogen, methyl, benzyl or acetyl,
$R_5$ is hydrogen or $C_1$–$C_4$alkyl, and
$R_6$ and $R_7$ are hydrogen.

4. A compound according to claim 1, wherein
$R_1$ is hydrogen or methyl,
$R_2$ is $C_1$–$C_6$alkyl, allyl, methallyl or benzyl,
$R_3$ is benzyl, and
Z is a group of the formula II or III,
$R_4$ is hydrogen or methyl, and
$R_5$, $R_6$ and $R_7$ are hydrogen.

5. Bis-[2-(2,2,6,6-tetramethyl-1-piperidinyl)-ethyl] dibenzylmalonate according to claim 1.

* * * * *